(12) United States Patent
Okawa et al.

(10) Patent No.: US 8,013,094 B2
(45) Date of Patent: *Sep. 6, 2011

(54) GELLING AGENTS AND GELATINOUS COMPOSITIONS

(75) Inventors: Tadashi Okawa, Ichihara (JP); Tomohiro Iimura, Sodegaura (JP)

(73) Assignee: Dow Corning Toray Company, Ltd., Chiyoda-Ku, Tokyo (JP)

( * ) Notice: Subject to any disclaimer, the term of this patent is extended or adjusted under 35 U.S.C. 154(b) by 319 days.

This patent is subject to a terminal disclaimer.

(21) Appl. No.: 11/993,372

(22) PCT Filed: Jun. 21, 2006

(86) PCT No.: PCT/JP2006/312849
§ 371 (c)(1),
(2), (4) Date: May 6, 2009

(87) PCT Pub. No.: WO2006/137577
PCT Pub. Date: Dec. 28, 2006

(65) Prior Publication Data
US 2010/0029862 A1 Feb. 4, 2010

(30) Foreign Application Priority Data

Jun. 21, 2005 (JP) ................. 2005-180066
Jun. 21, 2005 (JP) ................. 2005-180072
Jun. 16, 2006 (JP) ................. 2006-166880

(51) Int. Cl.
C08G 77/00 (2006.01)
(52) U.S. Cl. .......... 528/10; 528/41; 528/271; 528/275; 524/588
(58) Field of Classification Search .................. 524/588
See application file for complete search history.

(56) References Cited

U.S. PATENT DOCUMENTS

| | | | |
|---|---|---|---|
| 5,194,251 A | 3/1993 | Halloran et al. | |
| 6,110,230 A | 8/2000 | Friedrich et al. | |
| 6,468,512 B1 * | 10/2002 | Carmody | 424/65 |

FOREIGN PATENT DOCUMENTS

| | | | |
|---|---|---|---|
| EP | 0095676 A2 | | 12/1983 |
| EP | 0824656 A2 * | | 5/1998 |
| EP | 0842656 A2 | | 5/1998 |
| EP | 0842656 A2 * | | 5/1998 |
| EP | WO 2006137576 A1 | | 12/2006 |
| JP | 02243612 A2 | | 9/1990 |
| JP | 07215817 A | | 8/1995 |
| JP | 08012524 A | | 1/1996 |
| JP | 08012545 A | | 1/1996 |
| JP | 08012546 A | | 1/1996 |
| JP | 08109263 A | | 4/1996 |
| JP | 09241511 A | | 9/1997 |
| JP | 10158150 A | | 6/1998 |
| JP | 10036219 A | | 10/1998 |
| JP | 11193331 A | | 7/1999 |
| JP | 2000063225 A | | 2/2000 |
| JP | 2000281523 A | | 10/2000 |
| WO | WO 2005063856 A | | 7/2005 |
| WO | WO 2006137577 A2 | | 12/2006 |

OTHER PUBLICATIONS

PCT International Search Report for PCT/JP2006/312849, Dec. 21, 2006, 3 pages.
English language abstract for EP0842656, extracted from espacenet.com, Sep. 23, 2008.
English language abstract for JP 02243612, extracted from PAJ database, Sep. 30, 2008.
English language translation and abstract for JP07215817, extracted from searching PAJ, Sep. 23, 2008, 42 pages.
English language translation and abstract for JP08012545, extracted from searching PAJ, Sep. 30, 2008, 30 pages.
English language translation and abstract for JP08012546, extracted from searching PAJ, Sep. 30, 2008, 32 pages.
English language translation and abstract for JP08109263, extracted from searching PAJ, Sep. 30, 2008, 68 pages.
English language translation and abstract for JP09241511, extracted from searching PAJ, Sep. 30, 2008, 37 pages.
English language translation and abstract for JP10036219, extracted from searching PAJ, Sep. 30, 2008, 43 pages.
English language translation and abstract for JP10158150, extracted from searching PAJ, Sep. 23, 2008, 51 pages.
English language translation and abstract for JP11193331, extracted from searching PAJ, Sep. 30, 2008, 59 pages.
English language translation and abstract for JP2000063225, extracted from searching PAJ, Sep. 30, 2008, 75 pages.
English language translation and abstract for JP2000281523, extracted from searching PAJ, Oct. 3, 2008, 109 pages.
English language translation and abstract for JP2003226611, extracted from searching PAJ, Sep. 30, 2008, 81 pages.
English language abstract for WO2005063856, extracted from espacenet.com, Sep. 23, 2008.
PCT International Search Report PCT/JP2006/312848, dated Oct. 23, 2006, 4 pages.

* cited by examiner

*Primary Examiner* — Randy Gulakowski
*Assistant Examiner* — Lindsay Nelson
(74) *Attorney, Agent, or Firm* — Howard & Howard Attorneys PLLC

(57) ABSTRACT

A gelling agent comprising an organopolysiloxane having a silicon-bonded organic group represented by general formula: $R^1-X-CO-NH-[X-N(-CO-X-R^1)]_p-X-$ (1) (wherein $R^1$ designates a group containing metal salt of a carboxylic acid represented by formula $-COO^-(M^{n+})_{1/n}$ (where M is a metal that has a valence of 1 or higher); X's designate the same or different $C_2$ to $C_{14}$ bivalent hydrocarbon groups; and p designates an integer from 0 to 10.). Preferably, the organosiloxane has an optionally substituted $C_9$ or more univalent hydrocarbon group. And a gelatinous composition comprising:
(A) 1 to 99 wt. % of aforementioned gelling agent; and (B) 99 to 1 wt. % of a compound selected from the group consisting of a silicone oil, a no-polar organic compound, or a low-polar organic compound, or mixtures thereof. The gelatinous composition has excellent thermal stability, temporal stability, and properties of thixotropic rheology.

14 Claims, 3 Drawing Sheets

[Figure 1.]
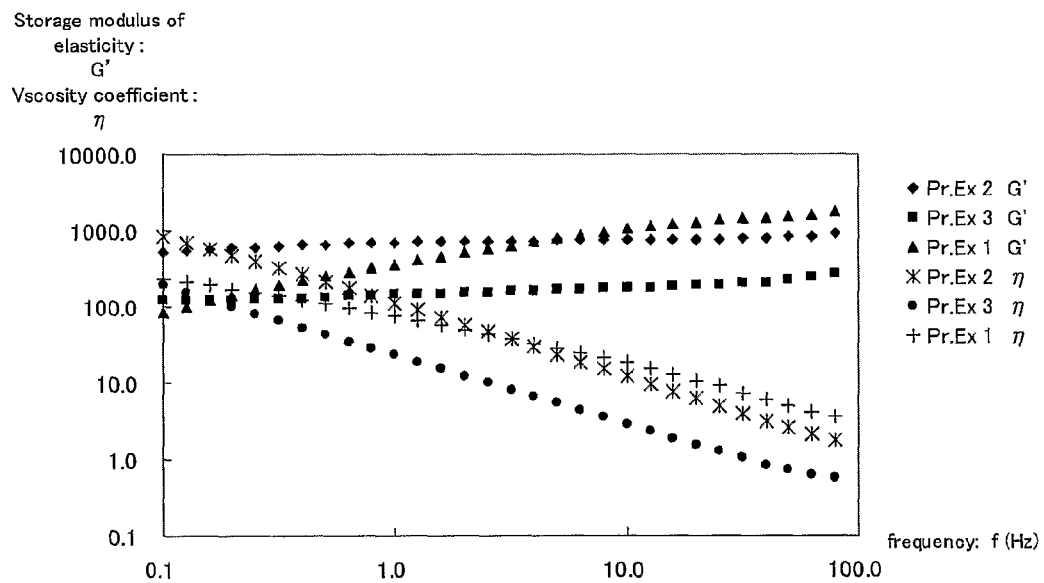
[Figure 2.]
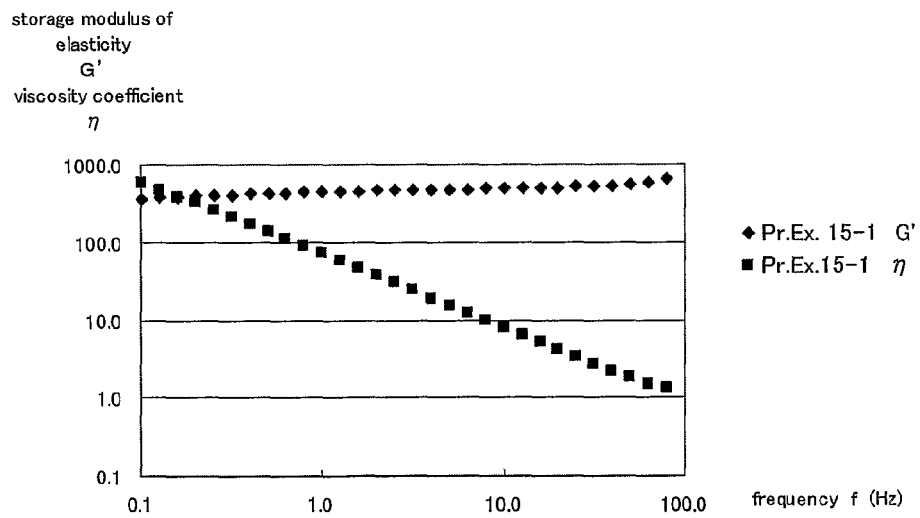

[Figure 3.]
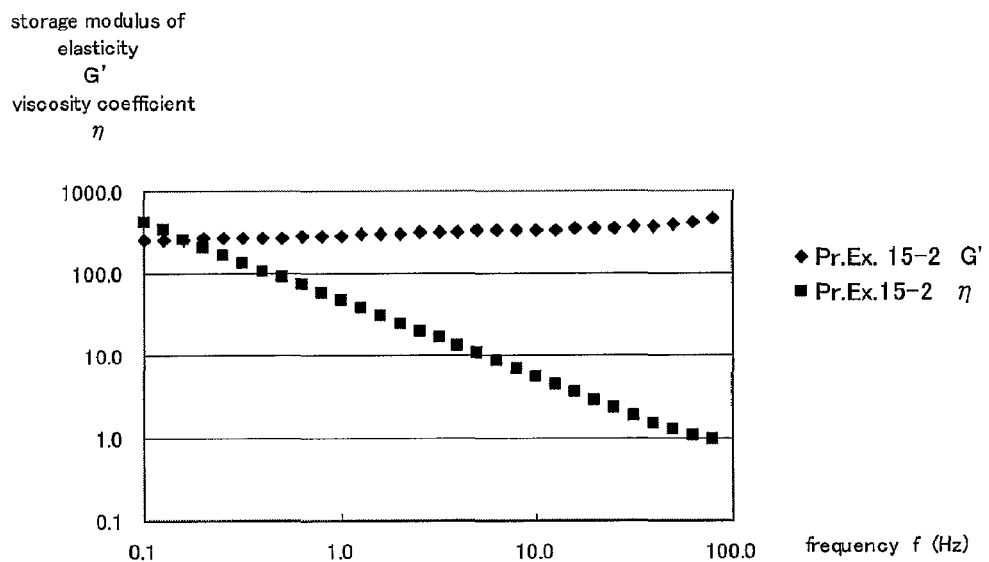
[Figure 4.]
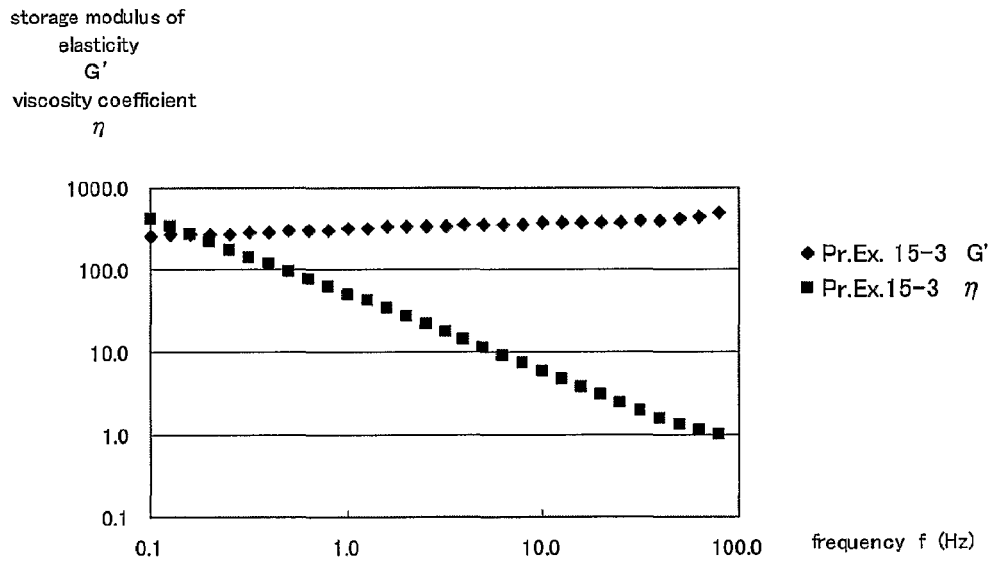

[Figure 5.]
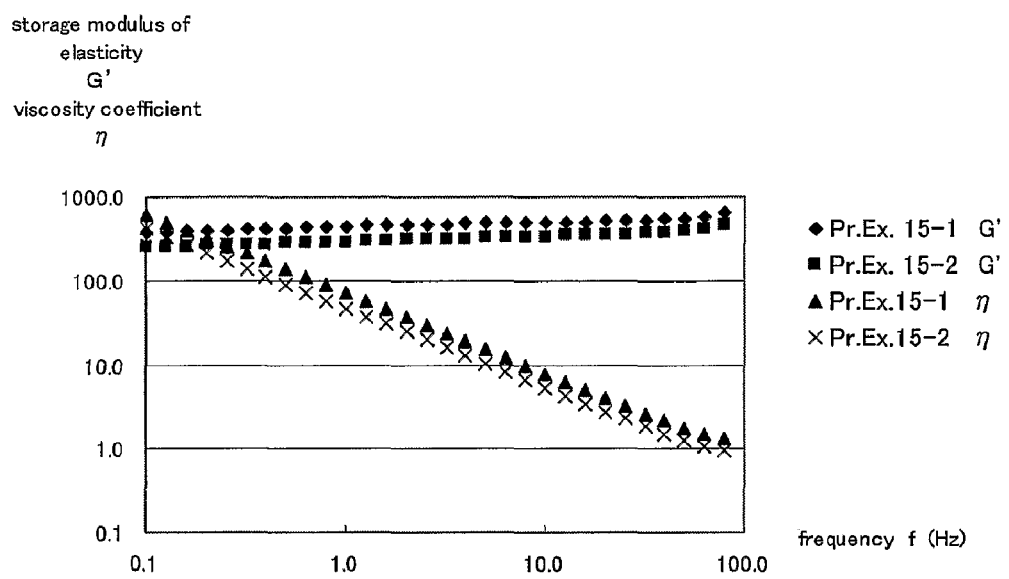

GELLING AGENTS AND GELATINOUS COMPOSITIONS

RELATED APPLICATIONS

This application claims priority to and all the advantages of International Patent Application No. PCT/JP2006/312849, filed on Jun. 21, 2006, which claims priority to Japanese Patent Application No. JP2005-180066, filed on Jun. 21, 2005, Japanese Patent Application No. JP2005-180072, filed on Jun. 21, 2005, and Japanese Patent Application No. JP2006-166880, filed on Jun. 16, 2006.

FIELD OF THE INVENTION

The present invention relates to gelling agents for silicone oils, low-polarity organic compounds, or non-polar organic compounds. The invention also relates to compositions composed of the aforementioned gelling agent, and silicone oil, low-polarity organic compound, or non-polar organic compound, and more specifically, to gelatinous compositions used in conjunction with dyes, inks, lubricating oils, agricultural substances, marine products, cosmetic substances, fibers, resins, polymers, rubbers, metals, etc.

BACKGROUND OF THE INVENTION

Gelling agents capable of gelling various types of organic liquids are known as alkali-metal salts or alkali-earth-metal salts of higher fatty acids, 1,2-hydroxy stearic acids, dibenzylidene sorbitols, amino acid derivatives, amide or urea compounds, etc. However, these known gelling agents are poorly compatible with silicone oils and therefore are unsuitable for gelling silicones. Moreover, the use of such gelling agents is limited only to those applications where they can provide stable gelling of both silicone oils and fats.

Due to such properties as excellent spreadability, ability of imparting a refreshed feel, lubricity, hydrophilicity, stability, etc., silicone oils (in particular low-viscosity silicone oils) find wide application, especially in cosmetic products. However, silicone oils are usually poorly compatible with other oils, and therefore cannot provide stability of products that contain such combinations. For example, it is impossible to provide stability in situations where wax is added for obtaining a gel product based on low-viscosity silicone oils. Another problem associated with such products is a turbid appearance. Replacement of waxes with a cross-linked silicone imparts to the product a feel of stickiness and eliminates the original feel of freshness inherent in silicone oils. Japanese Laid-Open Patent Application Publication (Kokai) H7-215817 discloses t discloses a silicone-oil gelling agent in the form of a polyether-graft type organopolysiloxane, but the gelling agent requires the simultaneous addition of an appropriate amount of water, and the obtained composition is not stable with time and is not completely satisfactory with regard to feel in use.

Japanese Laid-Open Patent Application Publication (Kokai) H10-158150 discloses the use of carboxamide polysiloxanes in cosmetic preparations, as well as in skin-care and hair-care compositions as aqueous emulsions of carboxamide polysiloxanes. However, the aforementioned publication does not teach that the organopolysiloxanes that contain carboxyamide groups can be used as gelling agents for silicone oils, non-polar organic compounds, or low-polarity organic compounds. Japanese Laid-Open Patent Application Publication (Kokai) H08-109263 describes the use of organo(poly)siloxane modified with polyvalent metal carboxylate as a gelling agent of silicone oils and shows the use of this agent in cosmetic products. Nevertheless, the gel composition having sufficient viscous property and a modulus of elasticity cannot be obtained without using this gelling agent in large quantities.

PCT publication WO2005/063856 discloses gelling agents as an organopolysiloxane having a silicon-bonded organic group containing amino alcohol salt of a carboxylic acid. However, these gelling agents and gelatinous composition prepared with those gelling agents have poor resistance to heat. E.g., when the gelling agents or cosmetics containing these gelling agents are stood at high temperature for several hours in the manufacturing process, the desired gelling properties may be lacked after cooling for the dehydration reaction under high temperature. In addition, the aforementioned PCT publication discloses only methylpolysiloxane having a silicon-bonded organic group containing amino alcohol salt of a carboxylic acid. Such organically-modified methylpolysiloxane have poor solubility in organic oils containing many alkyl groups. For this, such gelling agents do not have sufficient and general-purpose property to obtain stable gelatinous composition comprising many kinds of organic oils, especially in cosmetics.

SUMMARY OF THE INVENTION

The present invention provides a gelling agent suitable for gelling silicone oils, low-polarity liquid organic compounds and/or non-polar liquid organic compounds without the use of water. The obtained gelatinous composition of the present invention is characterized by excellent thermal stability, temporal stability, and having properties of thixotropic rheology.

The inventors herein have found that the aforementioned objects can be achieved by using a gelling agent comprising an organopolysiloxane having a silicon-bonded organic group represented by general formula (1):

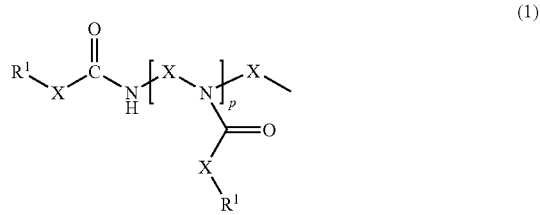

wherein $R^1$ designates a group containing metal salt of a carboxylic acid represented by formula $—COO^- \ (M^{n+})_{1/n}$ (where M is a metal that has a valence of 1 or higher, and n is the valence of M); X's designate the same or different $C_2$–$C_{14}$ bivalent hydrocarbon groups; and p designates an integer from 0 to 10, and by using a gelatinous composition that consists of 1 to 99 wt. % of a gelling agent (A) and 99 to 1 wt. % of a compound selected from the group consisting of a silicone oil, a non-polar organic compound, or a low-polarity organic compound (B).

Furthermore, the inventors have found that the aforementioned objects can be more preferably achieved by using a gelling agent comprising an organopolysiloxane having a silicon-bonded organic group represented by general formula (1) and an optionally substituted $C_9$ or more univalent hydrocarbon group.

The gelling agent of the present invention possesses high gelling capacity and can be used for gelling silicone oils, in particular, hydrophobic silicone oils and non-polar liquid organic compounds, without the use of water. Especially, the gelling agent of the organopolysiloxane having an optionally substituted $C_9$ or more univalent hydrocarbon group possesses excellent gelling capacity to a non-polar organic compound or a low-polarity organic compound having many alkyl groups for its solubility in these organic compounds. The gelatinous composition of the present invention possesses excellent thixotropic rheologic properties, temporal stability, and thermal stability.

BRIEF DESCRIPTION OF THE DRAWINGS

[FIG. 1] is the viscoelastic properties of gelatinous compositions obtained in Practical Example 1, Practical Example 2, and Practical Example 3.

[FIG. 2] is the viscoelastic properties of gelatinous compositions obtained in Practical Example 15-1.

[FIG. 3] is the viscoelastic properties of gelatinous compositions obtained in Practical Example 15-2.

[FIG. 4] is the viscoelastic properties of gelatinous compositions obtained in Practical Example 15-3.

[FIG. 5] is the viscoelastic properties of gelatinous compositions obtained in Practical Example 15-1 and Practical Example 15-2.

DETAILED DESCRIPTION OF THE INVENTION

The gelling agent of this invention is an organopolysiloxane having a silicon-bonded organic group represented by general formula (1):

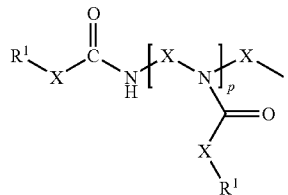

(1)

wherein $R^1$ designates a group containing metal salt of a carboxylic acid represented by formula $—COO^- (M^{n+})_{1/n}$ (where M is a metal that has a valence of 1 or higher, and n is the valence of M); X's designate the same or different bivalent hydrocarbon groups having $C_2$ to $C_{14}$; and p designates an integer from 0 to 10. The organic groups of general formula (1) can be exemplified by specific groups of the following formulae, where M designates a metal that has a valence of 1 or higher, and n is the valence of M:

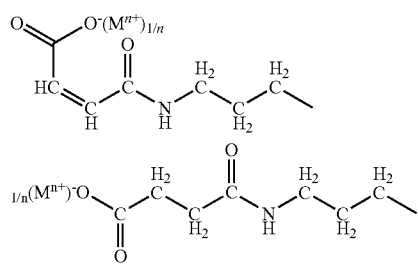

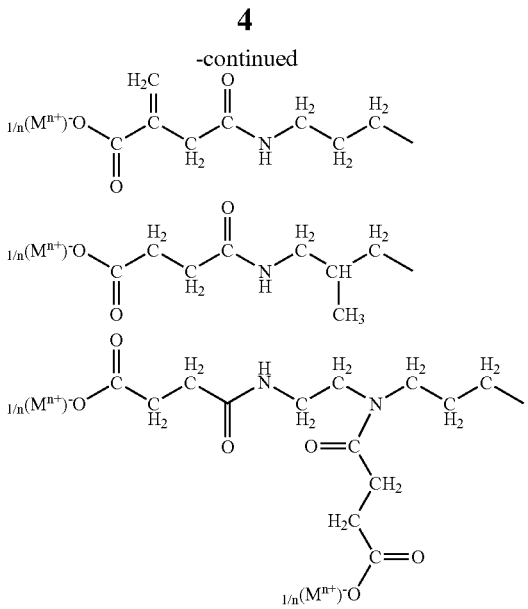

The organopolysiloxane having a silicon-bonded organic group of general formula (1) contains at least one of the siloxane units represented by the following formula (4) or (5):

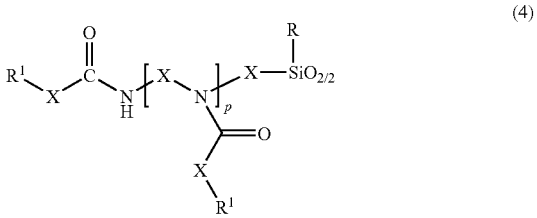

(4)

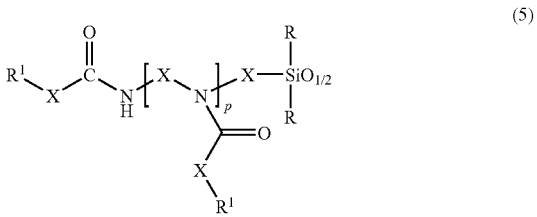

(5)

In these formulae, R designates an optionally substituted $C_1$ to $C_8$ univalent hydrocarbon group (except for the organic group represented by general formula (1)); R1, X and p are the same as define above.

Furthermore, the preferable gelling agent of this invention is an organopolysiloxane having an aforementioned silicon-bonded organic group represented by general formula (1) (—Y) and a silicon-bonded optionally substituted $C_9$ or more univalent hydrocarbon group (—Z). Containing such "long-chain" univalent hydrocarbon group and aforementioned organic group represented by general formula (1) within a molecule makes it possible to increase the solubility of the organopolysiloxane to a non-polar organic compound or a low-polarity organic compound having many alkyl groups.

Such silicon-bonded optionally substituted $C_9$ or more univalent hydrocarbon group (—Z) may be same or identical to each other. This univalent hydrocarbon group (—Z) may have a linear-chain, or a branched molecular structure. Having a linear-chain structure is preferable. The non-substituted univalent hydrocarbon groups can be exemplified by $C_9$ or more, preferably $C_9$ to $C_{1000}$ alkyl groups, aryl groups or aralkyl groups. The substituted univalent hydrocarbon groups can be exemplified by $C_9$ or more, preferably $C_9$ to $C_{1000}$ perfluoroalkyl groups, aminoalkyl groups, amidoalkyl groups {except for the organic groups represented by general formula (1)} or carbinol groups. Most preferable univalent hydrocarbon group (—Z) is $C_{10}$ to $C_{45}$ alkyl groups represented by the formula: —$(CH_2)_v$—$CH_3$ (v is an integer in the range of 9 to 44).

The organopolysiloxane having a silicon-bonded organic group of general formula (1) (—Y) and silicon-bonded an optionally substituted $C_9$ or more univalent hydrocarbon group (—Z) contains at least one of the aforementioned siloxane units represented by the following formula (4) or (5) and at least one of the siloxane units represented by the following formula (6) or (7):

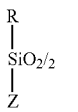

(6)

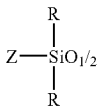

(7)

In these formulae, —R designates an optionally substituted $C_1$ to $C_8$ univalent hydrocarbon group {except for the organic group represented by general formula (1)}, —Z designates an aforementioned optionally substituted $C_9$ or more univalent hydrocarbon group {except for the organic group represented by general formula (1)}.

The gelling agent of the present invention may also consist of the following four types of siloxane units: $R_3SiO_{1/2}$, $R_2SiO_{2/2}$, $RSiO_{3/2}$, and $SiO_{4/2}$, where the R designate optionally substituted $C_1$ to $C_8$ univalent hydrocarbon groups. The non-substituted univalent hydrocarbon groups can be represented by methyl, ethyl, propyl, or similar alkyl groups; phenyl, tolyl, xylyl, or similar aryl groups; or aralkyl groups. The substituted univalent hydrocarbon groups can be represented by 3,3,3-trifluoropropyl, 3,3,4,4,4-pentafluyorobutyl, or similar perfluoroalkyl groups; 3-aminopropyl, 3-(aminoethyl)aminopropyl, or similar aminoalkyl groups; acetylaminoalkyl, or similar amidoalkyl groups {except for the organic groups represented by general formula (1)}. A part of R may be substituted with an alkoxy group. The alkoxy group may be exemplified by a methoxy, ethoxy, or a propoxy group. Typically R is an alkyl groups of $C_1$ to $C_6$, in particular, methyl group.

The organopolysiloxane that has a silicon-bonded organic group of general formula (1) may contain in one molecule at least one siloxane unit of formula (4) or (5). However, from the point of view of better gelling properties, it is preferable to have two or more such units. For the same purpose as above, it is preferable that the siloxane units of formula (4) or (5) be used in an amount of 0.1 to 50 mole %, more preferably 0.5 to 30 mole % of all soloxane units.

Furthermore, the organopolysiloxane having a silicon-bonded organic group of general formula (1) (—Y) and silicon-bonded an optionally substituted $C_9$ or more univalent hydrocarbon group (—Z) may contain in one molecule at least one siloxane unit of formula (4) or (5), and at least one siloxane units of formula (6) or (7). However, from the point of view of better solubility of the organopolysiloxane to organic compounds having many alkyl groups, it is preferable to have two or more such siloxane units of formula (6) or (7). For the same purpose as above, it is preferable that the siloxane units of formula (6) or (7) is used in an amount of 0.1 to 75 mole %, more preferably 5 to 30 mole % of all soloxane units.

The organopolysiloxane that has a silicon-bonded organic group of general formula (1) may contain in one molecule at least one organic group of formula (1). However, from the point of view of better gelling properties, it is preferable to have two or more such groups in an amount of more than 0.5 wt. %, and preferably more than 1.0 wt. %. The aforementioned organopolysiloxane may have a linear, branched, or cyclic molecular structure, of which the linear molecular structure is preferable. There are no restrictions with regard to the bonding position of the organic group of formula (1). When the aforementioned organopolysiloxane has a linear or a branched molecular structure, the organic group of formula (1) can be bonded to molecular terminals or to the sides of the molecular chains on the organopolysiloxane. Bonding to the sides of the molecular chains on the organopolysiloxane is preferable.

Furthermore, from the point of view of better gelling properties and solubility to organic compounds having many alkyl groups, it is preferable to have at least one, more preferably two or more silicon-bonded optionally substituted $C_9$ or more univalent hydrocarbon groups (—Z) in the aforementioned organopolysiloxane. When the aforementioned organopolysiloxane has a linear or a branched molecular structure, the optionally substituted $C_9$ or more univalent hydrocarbon groups (—Z) can be bonded to molecular terminals or to the sides of the molecular chains on the organopolysiloxane. Bonding to the sides of the molecular chains on the organopolysiloxane is preferable.

A representative linear organopolysiloxane having a silicon-bonded organic group of formula (1) is represented by the following general formula (2);

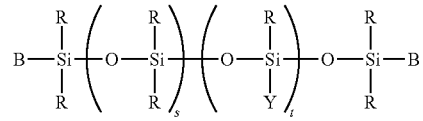

(2)

Wherein R designates the same as defined above, Y designates an organic group of general formula (1), and B is R or Y. When t=0, at least one of the two B's is Y. Above "s" designates an integer in the range of 10 to 100,000, preferable in the range of 100 to 10,000; "t" designates an integer between 0 and 50, preferably 1 to 30. It is recommended that t/(s+t) is in the range of 0.001 to 0.05, preferably 0.001 to 0.03. At room temperature, the organopolysiloxane having a silicon-bonded organic group of general formula (1) may comprise a viscous liquid having a turbidity from microscopic to white, or it may comprise a paste-like or a solid substance. The paste-like or solid state at room temperature is preferable.

In similar manner, a representative linear organopolysiloxane having a silicon-bonded organic group of general formula (1) (—Y) and a silicon-bonded optionally substituted $C_9$ or more univalent hydrocarbon group (—Z) is represented by the following general formula (3).

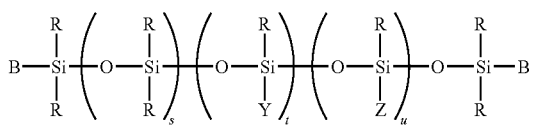

(3)

Wherein R is the same as defined above, Y is an organic group of general formula (1), and B is R, Y or Z. When t=0, at least one of the two B's is Y. When u=0, at least one of the two B's is Z. When t=0 and u=0, one of the two B's is Y and another is Z. Above "s" designates an integer in the range of 10 to 100,000, preferable in the range of 100 to 10,000; "t" designates an integer between 0 and 50, preferably 1 to 30, and "u" designates an integer between 0 and 1000, preferably 5 to 200. It is recommended that t/(s+t+u) is in the range of 0.001 to 0.05, preferably 0.001 to 0.03 and that u/(s+t+u) is in the range of 0.01 to 0.75, preferably 0.05 to 0.30. Furthermore, it is recommended that (s+t+u) is in the range of 20 to 5,000 from the point of view of better gelling properties and handling property as a raw material. At room temperature, the organopolysiloxane having a silicon-bonded organic group of general formula (1) (—Y) and a silicon-bonded optionally substituted $C_9$ or more univalent hydrocarbon group (—Z) may comprise a viscous liquid having a turbidity from microscopic to white, or it may comprise a paste-like or a solid substance. The paste-like or solid state at room temperature is preferable.

The organopolysiloxane having a silicon-bonded organic group of formula (1) can be prepared, e.g., by reacting an organopolysiloxane having a silicon-bonded organic group of general formula (8) and a metal compound of formula (9) given as below:

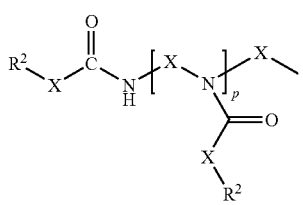

(8)

(where $R^2$ is a carboxylic group represented by formula —COOH or an ester carboxylate group represented by formula —COOR$^4$; $R^4$ is a univalent hydrocarbon group having C1 to C10; X's designate the same or different bivalent hydrocarbon groups having $C_2$ to $C_{14}$; and p designates an integer from 0 to 10.);

$$(M^{n+})j(L^{j-})n \qquad (9)$$

(where M is a metal that has a valence of 1 or higher; L is an oxygen atom or an anion; n is the valence of M; and j is the valence of L).

The organopolysiloxane having the organic group of aforementioned general formula (8) can be typically prepared by reacting an amine functional organopolysiloxane with a cyclic carboxylic acid anhydride. The aforementioned amino-functional organopolysiloxane can be exemplified by an organopolysiloxane having an amino group bonded to silicon via a bifunctional hydrocarbon group, and an organopolysiloxane having a silicon-bonded organic group of general formula (10):

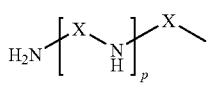

(10)

(where X's designate the same or different bivalent hydrocarbon groups having $C_2$ to $C_{14}$; and p designates an integer from 0 to 10. Normally, the bivalent hydrocarbon group X is an alkylene group, preferably a $C_2$ to $C_6$ alkylene group, and, more preferably, an ethylene group or a propylene group)

Cyclic carboxylic acid anhydrides useful to prepare the carboxyamide organopolysiloxane are illustrated by the following representative list: succinic acid anhydride, maleic acid anhydride, itaconic acid anhydride, citraconic acid anhydride, allylsuccinic acid anhydride, phthalic acid anhydride, norbornane-dicarboxylic acid anhydride, cyclohexane-dicarboxylic acid anhydride, nonenylsuccinic acid anhydride, and decenylsuccinic acid anhydride. Among these, the succinic acid anhydride is most preferable as it provides high gelling capacity and high transparency in gelatinous compositions. The reaction between amine groups contained in organopolysiloxanes and cyclic carboxylic acid anhydrides are known. In the presence of non-solvents or appropriate solvents, such reactions precede exothermically. A mole ratio between the first-mentioned amine groups and the second-mentioned carboxylic acid anhydride can be arbitrarily chosen, but if the amount of residual amine groups is too high, the gel-like product becomes tacky, and the gelling capacity is reduced. Typically, a ratio of the carboxylic acid anhydride to amine groups on the organopolysiloxane range from 0.5 to 1, preferably from 0.9 to 1.

Organic groups represented by formula (8), that can be prepared as above-described method, can be exemplified by compounds of the following formulae:

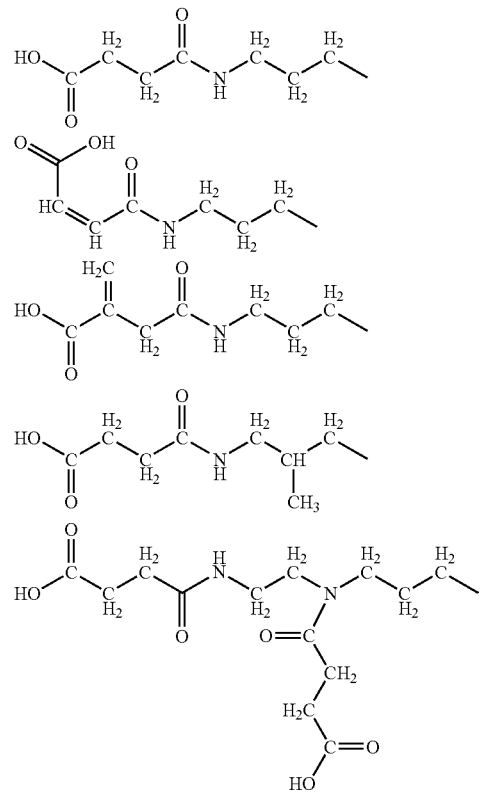

The terminal carboxyl or ester carboxylate group of an organic group represented by formula (8) can be converted into an organic group of formula (1) that comprises a metal salt of a carboxylic acid represented by formula —COO$^-$ $(M^{n+})_{1/n}$ (where M is a metal having a valence of 1 or higher, and n is the valence of M) by reacting a metal compound of aforementioned general formula (9): $(M^{n+})j(L^{j-})_n$. Wherein M is a metal that has a valence of 1 or higher; L is an oxygen atom or an anion; n is the valence of M; and j is the valence of L. Metals represented by M may be exemplified by lithium, sodium, potassium, magnesium, calcium, barium, iron, cobalt, aluminum, nickel, copper, vanadium, molybdenum, niobium, zinc, tantalum, etc. Preferably, the metals represented by M are alkali metals such as sodium and potassium, alkali earth metals such as magnesium and calcium, and aluminum in view of transparency and stability of gelatinous compositions regarding this invention. Sodium and potassium are most suitable for using univalent alkali metals makes it possible to change flowability of the obtained gelatinous composition reversibly at the change of the temperature. In contrast, the organopolysiloxanes having organic groups with amino alcohol salts as gelling agents have poor resistance to heat. For this, when the gelling agents or cosmetics containing th gelling agents are stood at a temperature higher than 110° C. for several hours in the manufacturing process, the desired gelling properties may be lacked after cooling for the dehydration reaction under high temperature.

The following are specific examples of appropriate metal compounds: lithium hydroxide, sodium hydroxide, potassium hydroxide, magnesium hydroxide, calcium hydroxide, aluminum hydroxide, iron hydroxide, copper hydroxide, zinc hydroxide, or a similar metal hydroxide; methoxy lithium, methoxy sodium, methoxy potassium, ethoxy lithium, ethoxy sodium, ethoxy potassium, t-butoxy potassium, or a similar metal alcoholate; phenoxy lithium, phenoxy sodium, phenoxy potassium, paramethoxyphenoxy sodium, or a similar alkali metal arylate; lithium, sodium, potassium, or a similar alkali metal; lithium hydride, sodium hydride, potassium hydride, or a similar alkali metal hydride; methyl lithium, n-butyl lithium, sec-butyl lithium, t-butyl lithium, n-butyl sodium, n-butyl potassium, diethyl zinc, or a similar alkylmetal compound; phenyl lithium, phenyl sodium, potassium naphthalenide, or a similar optionally substituted aryl alkali metal; copper fluoride, potassium chloride, aluminum chloride, magnesium chloride, zinc chloride, iron chloride, copper chloride, titanium tetrachloride, calcium bromide, aluminum bromide, magnesium bromide, zinc bromide, iron bromide, or a similar metal halide; magnesium oxide, copper oxide, titanium oxide, zinc oxide, or a similar metal oxide; calcium carbonate, barium carbonate, copper carbonate, or similar metal carbonate; magnesium sulfate, potassium sulfate, zinc sulfate, iron sulfate, copper sulfate, aluminum sulfate, or a similar metal sulfate. Most preferable of the above metal compounds from the point of view of reactivity, cost, and workability are metal hydroxides, metal alcholates, and metal halides.

Reaction may also be carried out between metal compounds of formula (9) and an organopolysiloxane modified directly with carboxylic acid or with a carboxylic acid ester, but after formation of metal salts, reactions may occur between various metal compounds. Reaction conditions between metal compounds of general formula (9) and univalent and/or polyvalent metal salts of carboxylic acid, ester carboxylate, or carboxylic acid cannot be unequivocally prescribed for all cases since they depend on the type of the metal compound that participates in the reaction, but taking into account reactivity of the metal compounds, it is recommended to conduct the reaction by dispersing the metal compounds in appropriate media.

Normally, the reaction of forming an organic group of formula (1) that contains a carboxylic acid metal salt represented by formula $—COO^- (M^{n+})_{1/n}$ (where M is a metal of a valence equal to 1 or higher, and n is the valence of M) easily proceeds at a temperature in the range from room temperature to about 100° C. Although the reaction mole ratio between the carboxylic groups or ester carboxylate groups of organopolysiloxane that contains organic groups of formula (8) and the metal compounds of formula (9) may be arbitrary, it is recommended to have the aforementioned mole ratio in the range of 0.1 to 5.0, preferably 0.4 to 2.0. If the mole ratio of the reaction exceeds the upper recommended limit, the organopolysiloxane that has an organic group of formula (1) will not be able to demonstrate sufficient gelling properties. If, on the other hand, the aforementioned mole ratio is below the recommended lower limit, the reaction system will become strongly alkaline, especially in the case of a reaction with a basic metal compound, and this may break siloxane bonds of the organopolysiloxane and decrease stability of the obtained gel.

Only a part of a terminal carboxylic group or a terminal ester carboxylate of an organic group of general formula (8) can be neutralized by the metal compound of formula (9) $(M^{n+})_j(L^{j-})_n$ and converted into an organic group of general formula (1). The same method can be used for adjusting softness of the resulting gel. For example, an organopolysiloxane having an organic group of formula (8) and an organic group of formula (1) can be prepared by adding a metal compound of formula (9) $(M^{n+})_j(L^{j-})_n$, which amount is 80% neutral relative to the terminal carboxylic group or the terminal ester carboxylate of an organic group of general formula (8). A gel obtained with the use of the last-mentioned organopolysiloxane is softer by touch than a gel obtained with the use of an organopolysiloxane having an organic group of formula (1) prepared by adding a metal salt of formula (9) $(M^{n+})_j(L^{j-})_n$, which amount is 100% neutral to the terminal carboxylic group or the terminal ester carboxylate of an organic group of general formula (8).

In similar manner, the organopolysiloxane having a silicon-bonded organic group (—Y) of general formula (1) and a silicon-bonded optionally substituted $C_9$ or more univalent hydrocarbon group (—Z) can be prepared by reacting an organopolysiloxane having a silicon-bonded organic group of general formula (8) and a silicon-bonded optionally substituted $C_9$ or more univalent hydrocarbon group (—Z) with a metal compound of formula (9). Then, the organopolysiloxane having a silicon-bonded organic group of general formula (8) and a silicon-bonded optionally substituted $C_9$ or more univalent hydrocarbon group (—Z) with a metal compound of formula (9) can be typically prepared by reacting an amine functional organopolysiloxane having a silicon-bonded optionally substituted $C_9$ or more univalent hydrocarbon group (—Z) with a cyclic carboxylic acid anhydride as above.

The aforementioned amine functional organopolysiloxane having a silicon-bonded optionally substituted $C_9$ or more univalent hydrocarbon group (—Z) can be prepared by some known synthesis reaction. For example, such organopolysiloxane can be prepared by the hydrosilylation reaction between organohydrogenpolysiloxane, a compound having optionally substituted $C_9$ or more univalent hydrocarbon group and unsaturated hydrocarbon group within a molecule, and an amino-functional compound having unsaturated hydrocarbon group within a molecule.

Since the aforementioned organopolysiloxane having a silicon-bonded organic group (—Y) of general formula (1) has an excellent gelling properties by mixing it with a silicone oil, a non-polar organic compound, or a low-polarity organic compound under heating conditions with subsequent cooling to room temperature, it is suitable for use as a gelling agent for these compounds. Especially, the aforementioned organopolysiloxane having a silicon-bonded organic group (—Y) of general formula (1) and a silicon-bonded optionally substituted $C_9$ or more univalent hydrocarbon group (—Z) has an excellent gelling capacity to a non-polar organic compound or a low-polarity organic compound having many alkyl groups for its solubility in these organic compounds.

Since these organopolysiloxane gelling agent has low gelling capacity with regard to methanol, ethanol, or similar polar organic compounds, such solvents can be used in the preparation of the organopolysiloxane gelling agent. For example, a silicone oil or a non-polar liquid organic compound may be mixed with a polar organic compound, and an organopolysiloxane having an organic group of formula (8) and a metal compound of formula (9) are added to the aforementioned mixture. Then, neutralization reaction between the carboxyl groups of the carboxyamide-containing organopolysiloxane and a metal compound is carried out to produce the reaction product, an organopolysiloxane having an organic group of formula (1), in a liquid mixture. After removal of the aforementioned polar organic compound by distillation under reduced pressure, a gelatinous silicone oil or a gelled non-polar liquid organic compound is obtained.

A gelatinous composition of the invention is comprised of:
(A) 1 to 99 wt. % of a gelling agent of aforementioned organopolysiloxanes and
(B) 99 to 1 wt. % of a silicone oil, a non-polar organic compound, or a low-polarity organic compound (B) other than component (A).

In the gelatinous composition of the invention component (A) functions as a gelling agent of component (B). Each of a silicone oil, non-polar, or low-polarity organic compound of component (B) can be used independently, or may be mixed with two or three constituents such as silicone oils, non-polar organic compounds or low-polarity organic compounds. Components (A) and (B) should be mixed in a ratio within the range of (A):(B)=(1 to 99):(99 to 1) wt. %, preferably (2 to 40):(98 to 60) wt. %, and even more preferably (10 to 30):(90 to 70) wt. %.

The silicone oil should be one that is not contained in component (A) and may have a cyclic, linear-chain, or a branched molecular structure. In order to facilitate gelling, the use of a hydrophobic silicone oil is preferable and the oil should have a viscosity in the range of 0.65 to 100,000 mm$^2$/s, preferably in the range of 0.65 to 10,000 mm$^2$/s at 25° C. The following are specific examples of such oils: octamethylcyclotetrasiloxane, tetramethylcyclopentasiloxane, or a similar cyclic diorganopolysiloxane; hexamethyldisiloxane, dimethylpolysiloxane capped at both molecular terminals with trimethylsiloxy groups, methylphenylpolysiloxane capped at both molecular terminals with trimethylsiloxy groups, methylalkylpolysiloxane capped at both molecular terminals with trimethylsiloxy groups, or a similar linear-chain diorganopolysiloxane, methyl tristrimethylsiloxysilane, ethyl tristrimethylsiloxysilane, propyl tristrimethylsiloxysilane, tetrakis tristrimethylsiloxysilane, or a similar branched organopolysiloxane. Of these, preferable are volatile linear dimethylpolysiloxane, branched methylpolysiloxane and cyclic dimethylpolysiloxane, especially, decamethylcyclopentasiloxane.

The non-polar organic compounds or low-polarity organic compounds can be exemplified by the following: hexane, heptane, toluene, xylene, mesitylene, liquid paraffin, vaseline, n-paraffin, isoparaffin, isododecane, hydrogenated polyisobutylene, ozokerite, ceresin, squalane, pristine, or similar hydrocarbons; avocado oil, almond oil, olive oil, sesame oil, sasanqua oil, safflower oil, soybean oil, Camellia oil, corn oil, rapeseed oil, persic oil, castor oil, cottonseed oil, peanut oil, cacao oil, palm oil, palm kernel oil, Japan wax, coconut oil, or similar vegetable oils or fats; mink oil, egg yolk oil, beef tallow, and pork fat, hardened oil, or similar animal oils or fats; beeswax, carnauba wax, whale wax, lanolin, liquid lanolin, regenerated lanolin, hardened lanolin, candelilla wax, jojoba wax, microcrystalline wax, or a similar wax; palmityl alcohol, stearyl alcohol, oleyl alcohol, lanolin alcohol, cholesterol, phytosterol, 2-hexyldecanol, isostearyl alcohol, 2-octyldecanol, or a similar higher alcohol; methyl formate, ethyl formate, ethyl acetate, propyl acetate, butyl acetate, cetyl octate, isopropyl myristate, isopropyl palmitate, butyl stearate, hexyl laureate, myristyl myristate, olelyl oleate, decyl oleate, octyldecyl myristate, hexyldecyl dimethyloctanate, cetyl lactate, myristyl lactate, diethyl phthalate, dibutyl phthalate, lanolin acetate, ethylene glycol monostearate, propylene glycol monostearate, propylene glycol dioleate, glycerin monostearate, glycerin monooleate, glycerin tri-2-ethylenehexanate, trimethylolpropane, tri-2-ethylenehexanate, or a similar ester oil; triglyceride of a liquid fatty acid, and artificial skin (mixture of squalane with liquid fatty acid triglyceride, and oleic acid).

Especially, the aforementioned organopolysiloxane having a silicon-bonded organic group (—Y) of general formula (1) and a silicon-bonded optionally substituted $C_9$ or more univalent hydrocarbon group (—Z) has an excellent gelling capacity to a non-polar organic compound or a low-polarity organic compound having many alkyl groups for its solubility in these organic compounds. Such non-polar organic compounds or low-polarity organic compounds having many alkyl groups can be exemplified by the following: paraffin wax, vaseline, n-paraffin, hydrogenated polyisobutylene, ozokerite, ceresin, squalane, pristine, or similar hydrocarbons; avocado oil, almond oil, olive oil, sesame oil, sasanqua oil, safflower oil, soybean oil, Camellia oil, corn oil, rapeseed oil, persic oil, castor oil, cottonseed oil, peanut oil, cacao oil, palm oil, palm kernel oil, Japan wax, coconut oil, or similar vegetable oils or fats; mink oil, egg yolk oil, beef tallow, and pork fat, hardened oil, or similar animal oils or fats; beeswax, carnauba wax, whale wax, lanolin, liquid lanolin, regenerated lanolin, hardened lanolin, candelilla wax, jojoba wax, microcrystalline wax, or a similar wax; palmityl alcohol, stearyl alcohol, oleyl alcohol, lanolin alcohol, cholesterol, phytosterol, 2-hexyldecanol, isostearyl alcohol, 2-octyldecanol, or a similar higher alcohol; methyl formate, ethyl formate, ethyl acetate, propyl acetate, butyl acetate, cetyl octate, isopropyl myristate, isopropyl palmitate, butyl stearate, hexyl laureate, myristyl myristate, olelyl oleate, decyl oleate, octyldecyl myristate, hexyldecyl dimethyloctanate, cetyl lactate, myristyl lactate, diethyl phthalate, dibutyl phthalate, lanolin acetate, ethylene glycol monostearate, propylene glycol monostearate, propylene glycol dioleate, glycerin monostearate, glycerin monooleate, glycerin tri-2-ethylenehexanate, or a similar ester oil; triglyceride of a liquid fatty acid, and artificial skin (mixture of squalane with liquid fatty acid triglyceride, and oleic acid). As component (B) of this invention, these organic compounds may be combined with aforementioned silicone oil in a ratio within the range of (1 to 99) (99 to 1) wt. %.

The gelatinous composition of the present invention can be prepared by different methods. One method consists of mixing components (A) and (B). Another method consists of mixing an organopolysiloxane having in one molecule at least one carboxylic acid ester or a carboxylic acid of formula (5) with component (B) and a metal compound of formula (6): $(M^{n+})j(L^{j-})_n$ and then causing a neutralization reaction between the carboxyl groups of the carboxyamide-containing organopolysiloxane and a metal compound in component (B), or causing a neutralization reaction in a solvent. At room temperature the composition of this invention is in the state of a gel-like substance. It is understood that the gel characteristics of the composition may vary depending on the chemical structure of component (A), but at temperatures higher than 50° C., the composition normally turns into liquid.

Within the range that does not cause liquefaction at room temperature, the composition can be combined with water, or ethanol, ethyleneglycol, glycerin, or similar alcohols, phenols, amines, carboxylic acids, or other polar liquid organic compounds.

A gelatinous composition comprising components (A) and (B) can be obtained with excellent transparency by selecting appropriate organic groups of formula (1) that are contained in component (A), especially by selecting types and amounts of monovalent or polyvalent metal ion species, as well as types of silicon-bonded hydrocarbon radicals of component (A) and types of component (B). More specifically, the transparent gelatinous composition of an attractive appearance can be obtained by selecting types of bivalent hydrocarbon groups (—X—), values of "p" and/or types of metal ion $M^{n+}$ in the organic groups represented by formula (1) of component (A) and by selecting component (B) as a colorless, transparent, turbidity-free compound. To obtain a gelatinous composition of a transparent appearance, it is recommended that X is selected as an alkylene group, "p" as 0 or 1, metal ions $M^{n+}$ as sodium ions ($Na^+$), potassium ions ($K^+$), magnesium ion ($Mg^{2+}$), calcium ion ($Ca^{2+}$), or similar alkali metal ions, or similar alkali earth metal ions in the organic groups represented by formula (1); and that component (B) be comprised of dimethylpolysiloxane or methylpolysiloxane having a viscosity of 0.65 to 10,000 $mm^2/s$ at 25° C. The transparent gelatinous composition of this invention is recommended to have a refractive index in the range of 1.20 to 1.60, preferably 1.25 to 1.45.

EXAMPLES

The invention will be further described in more detail with reference to practical examples, though it should be understood that these examples should not be construed as limiting the scope of possible applications of the invention. In the examples, Me designates methyl groups. The following methods were used for measuring viscoelasticity and penetrability of the gel-like products.

[Refractive Index]
The refractive index of the gelatinous compositions was measured at 25° C. by means of an ABBE refractometer (Type ER-1) produced by ERMA Inc.

[Viscoelasticity Measurement]
This property was measured as storage elasticity G' (Pa) by changing conditions of strain (%). Measurement were carried out with the use of a dynamic viscoelasticity analyzer (RDA-700 Dynamic Analyzer of Rheometrics Inc.) by changing frequency (f) and maintaining deformation constant Measurements were carried out under the following conditions:
Sample diameter: 25 mm
Sample thickness: 1 mm
Deformation: 20%
Frequency (f): 0.1 Hz to 80 Hz Practical Example 1

A mixture was prepared from 30 g (11.0 mmol of NH2 groups) of a copolymer of methyl (3-aminopropyl) siloxane and dimethylpolysiloxane represented by the following average structural formula:

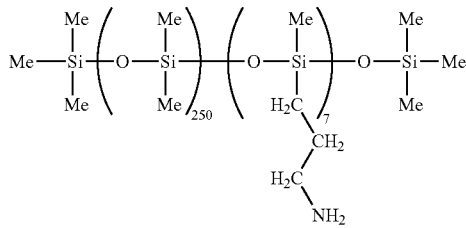

and 1.10 g (11.0 mmol) of an anhydrous succinic acid, which were both mixed in 36 g of isopropyl alcohol. The mixture was stirred for 5 hr at 30 to 35° C. Results of infrared (IR) analysis showed that specific absorption of carboxylic anhydride was lost, and that specific absorption of amide groups and carboxylic groups was detected. This confirmed that the obtained product was comprised of an modified methylpolysiloxane of the following average structural formula:

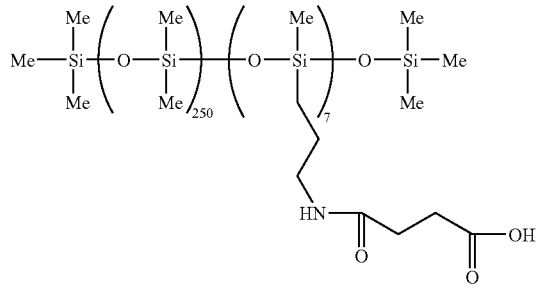

The obtained reaction product was further combined with 2.2 g (10.8 mmol) of a 20 wt. % aqueous solution of sodium hydroxide, and a reaction was carried out for 30 min. at 25° C. Following this, hexane was introduced and the solution was mixed uniformly. And, volatile contents were removed by distillation with heating in vacuum. As a result, a white solid substance was obtained. IR analysis showed that the obtained white solid substance was comprised of organically-modified methylpolysiloxane having carboxylic acid sodium salts on terminals of a silicon-bonded organic group and represented by the following formula:

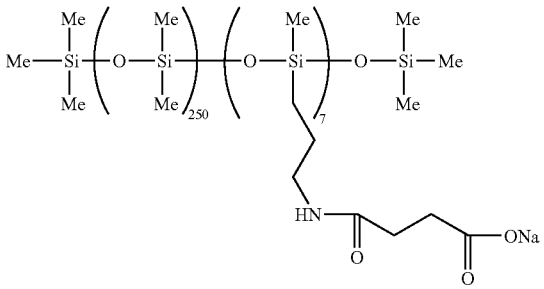

2 g of the obtained white solid substance (e.g. Gelling agent No. 1) and 18 g of decamethylpentacyclosiloxane were stirred at 90° C. Then, the mixed solution was cooled, and a transparent hard gelatinous composition was obtained. After being stored for 3 months at room temperature, the product remained transparent and gelatinous and thus showed good stability. The refractive index of the obtained gelatinous composition was equal to 1.3970.

Practical Example 2

A mixture was prepared from 10 g (2.82 mmol of $NH_2$ groups) of a copolymer of a methyl (3-2-aminoethyl aminopropyl)siloxane and dimethylpolysiloxane represented by the following average structural formula:

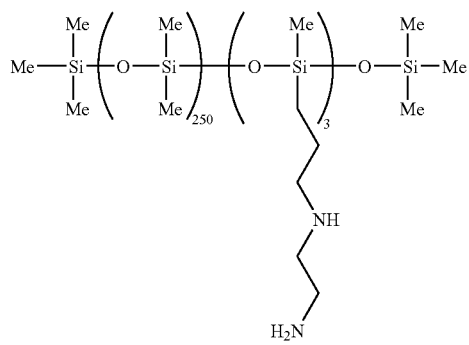

and 0.28 g (2.82 mmol) of an anhydrous succinic acid, which were both mixed in 20 g of isopropyl alcohol. The mixture was stirred for 5 hr at 30 to 40° C. Results of infrared (IR) analysis showed that specific absorption of carboxylic anhydride was lost, and that specific absorption of amide groups and carboxylic groups was detected. The obtained reaction product was cooled to the room temperature and further combined with 0.56 g (2.79 mmol) of a 20 wt. % aqueous solution of sodium hydroxide, and a reaction was carried out for 30 min. at room temperature. Following this, hexane was introduced and the solution was mixed uniformly. And, volatile contents were removed by distillation with heating in vacuum. As a result, a white solid substance was obtained. IR analysis showed that the obtained white solid substance was comprised of organically-modified methylpolysiloxane having carboxylic acid sodium salts on terminals of a silicon-bonded organic group and represented by the following formula:

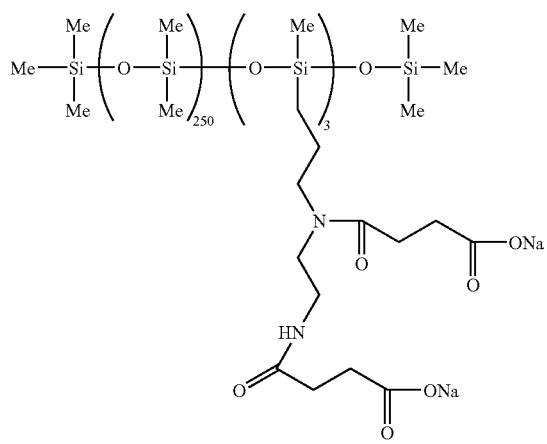

2 g of the obtained white solid substance (e.g. Gelling agent No. 2) and 18 g of decamethylpentacyclosiloxane were stirred at 90° C. Then, the mixed solution was cooled, and a transparent hard gelatinous composition was obtained (The content of the gelling agent was 10 wt. %.).

In a similar manner, 1.5 g of the obtained white solid substance (e.g. Gelling agent No. 2) and 18.5 g of decamethylpentacyclosiloxane were stirred, cooled to obtain a transparent gelatinous composition (The content of the gelling agent was 7.5 wt. %.), which was relatively soft as compared to the above gelatinous composition having a 10 wt. % content of the gelling agent. The refractive index of these obtained gelatinous compositions were equal to 1.3980.

Practical Example 3

A reaction and mixing was carried out under the same conditions as in Practical Example 2, but using 0.784 g (2.79 mmol) of 20 wt. % aqueous solution of potassium hydroxide in place of 20 wt. % aqueous solution of sodium hydroxide, and a white solid substance of an organically-modified methylpolysiloxane represented by the formula given below was obtained.

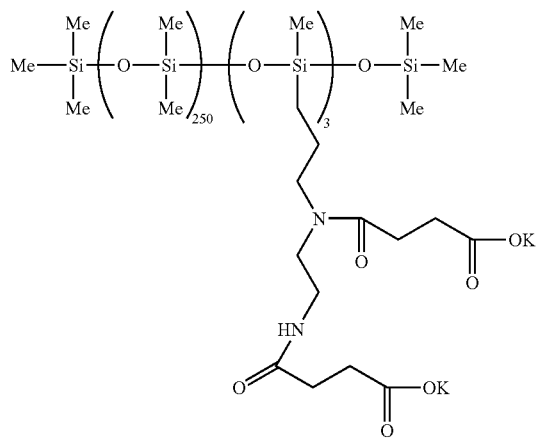

2 g of the obtained white solid substance (e.g. Gelling agent No. 3) and 18 g of decamethylpentacyclosiloxane were stirred at 90° C. Then, the mixed solution was cooled, and a transparent hard gelatinous composition was obtained. This gelatinous composition kept its transparency superior to that of the sodium-salt type composition obtained in Practical Example 2, and had the feel of a soft gel.

After being stored for 3 months at room temperature, the product remained transparent and gelatinous and thus showed good stability. The refractive index of the obtained gelatinous composition was equal to 1.3981.

Practical Example 4

A reaction and mixing was carried out under the same conditions as in Practical Example 2, but using 0.54 g (2.79 mmol) of 28 wt. % aqueous solution of sodium methoxide ($NaOCH_3$) in place of 20 wt. % aqueous solution of sodium hydroxide, and a white solid substance of an organically-modified methylpolysiloxane represented by the formula given as below was obtained.

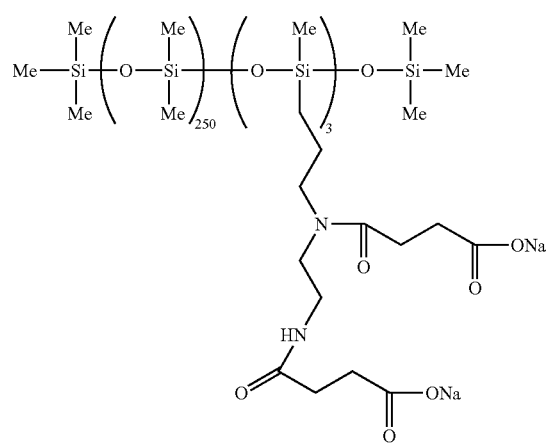

2 g of the obtained white solid substance (e.g. Gelling agent No. 4) and 18 g of decamethylpentacyclosiloxane were stirred at 90° C. Then, the mixed solution was cooled, and a transparent hard gelatinous composition was obtained.

Practical Example 5

A reaction and mixing was carried out under the same conditions as in Practical Example 2, but using 0.50 g (2.51 mmol, mole number of 90 wt. % with respect to neutralize of terminal carboxylic group) of 20 wt. % aqueous solution of sodium hydroxide in place of 0.56 g (2.79 mmol) of 20 wt. % aqueous solution of sodium hydroxide, a white solid substance as a mixture of organically-modified methylpolysiloxanes represented by the average structural formulae (i) to (iv) given as below was obtained.

(i)

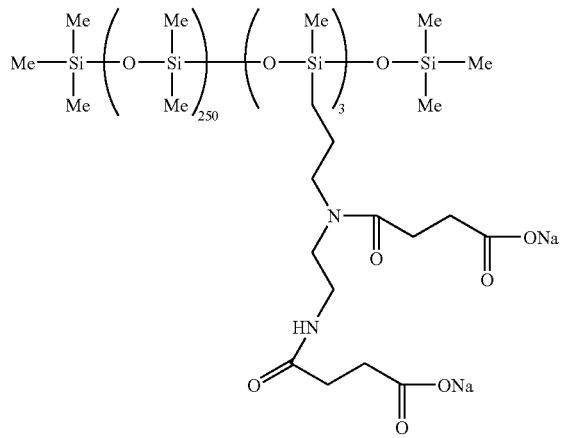

(ii)

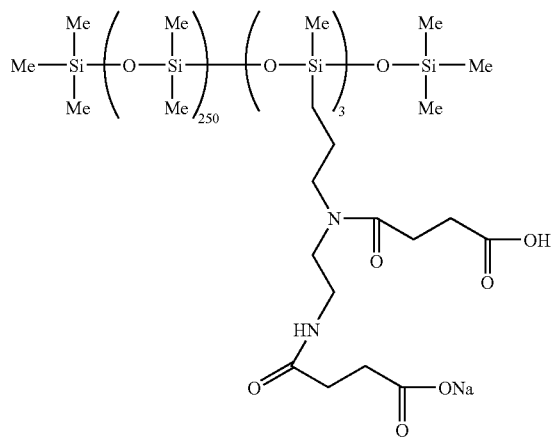

(iii)

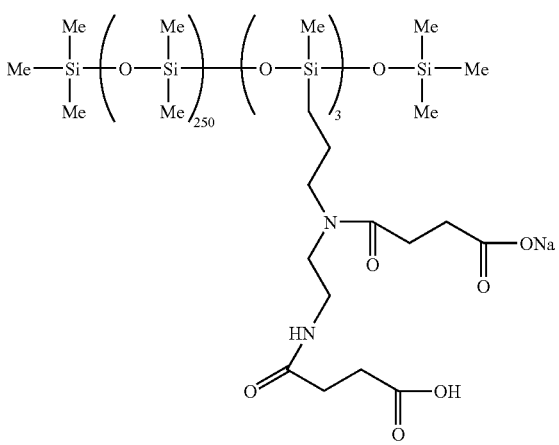

(iv)

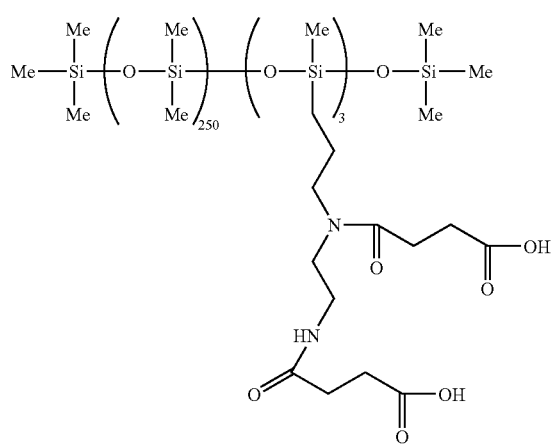

2 g of the obtained white solid substance (e.g. Gelling agent No. 5) and 18 g of decamethylpentacyclosiloxane were stirred at 90° C. Then, the mixed solution was cooled, and a transparent gelatinous composition was obtained. The gelatinous composition was relatively soft as compared to that obtained in the Practical Example 2. The refractive index of the obtained gelatinous composition was equal to 1.3980.

Practical Example 6

A mixture was prepared from the following components: 10 g of the organically-modified methylpolysiloxane obtained in Practical Example 1 having a sodium salt of a carboxylic acid on the molecular terminals of silicon-bonded organic groups; 10 g of isopropyl alcohol, 5 g of water, and 0.56 g of calcium chloride. The components were mixed for 4 hours with heating at 60° C. The reaction solution was combined with 200 g of hexane and water, and an inorganic salt formed in this process was washed. Then, the organic layer was removed, and a white solid substance of an organically-modified methylpolysiloxane represented by the formula given as below was obtained.

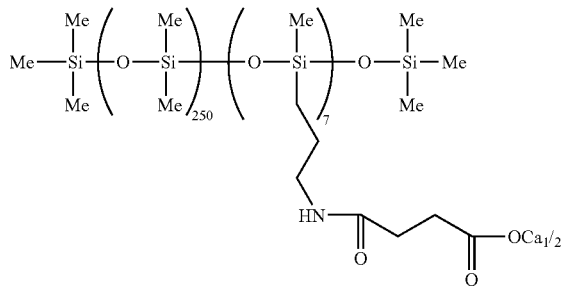

2 g of the obtained white solid substance (e.g. Gelling agent No. 6) and 18 g of decamethylpentacyclosiloxane were stirred at 90° C. Then, the mixed solution was cooled, and a transparent hard gelatinous composition was obtained. The refractive index of the obtained gelatinous composition was equal to 1.3978.

Practical Example 7

A mixture was prepared from 30 g (10.2 mmol of NH2 groups) of a copolymer of methyl (3-aminopropyl)siloxane and dimethylpolysiloxane represented by the following average structural formula:

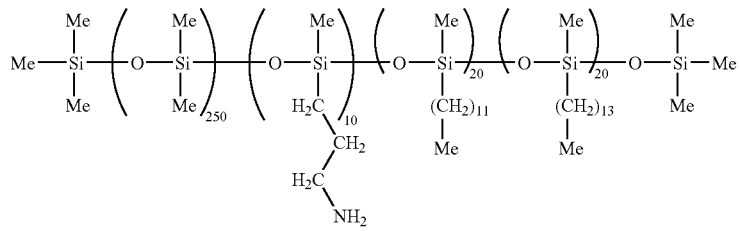

and 1.01 g (10.2 mmol) of an anhydrous succinic acid, which were both mixed in 36 g of isopropyl alcohol. The mixture was stirred for 5 hr at 30 to 35° C. Results of infrared (IR) analysis showed that specific absorption of carboxylic anhydride was lost, and that specific absorption of amide groups and carboxylic groups was detected. This confirmed that the obtained product was comprised of an modified methylpolysiloxane of the following average structural formula:

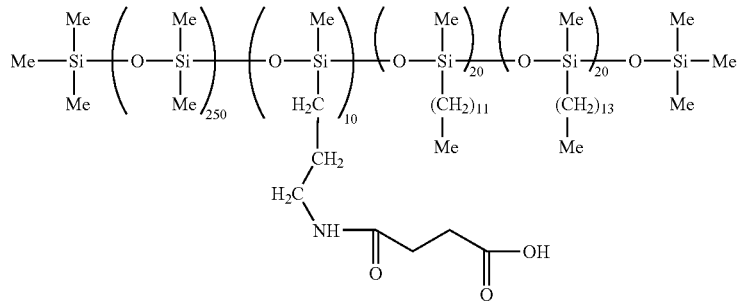

The obtained reaction product was further combined with 2.02 g (10.1 mmol) of a 20 wt. % aqueous solution of sodium hydroxide, and a reaction was carried out for 30 min. at 25° C. Following this, hexane was introduced and the solution was mixed uniformly. And, volatile contents were removed by distillation with heating in vacuum. As a result, a white solid substance was obtained. IR analysis showed that the obtained white solid substance was comprised of organically-modified methylpolysiloxane having carboxylic acid sodium salts on terminals of a silicon-bonded organic group and represented by the following formula:

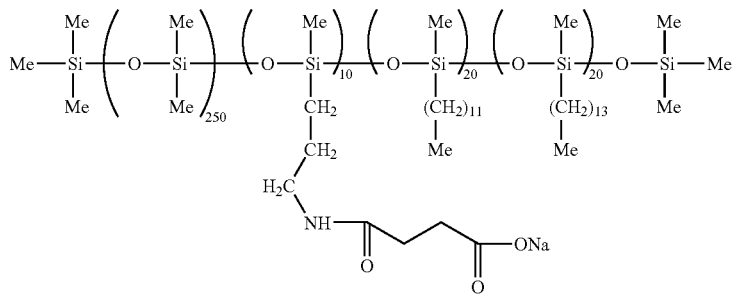

2 g of the obtained white solid substance (e.g. Gelling agent No. 7) and 18 g of liquid paraffin were stirred at 90° C. Then, the mixed solution was cooled, and a transparent hard gelatinous composition was obtained. After being stored for 3 months at room temperature, the product remained transparent and gelatinous and thus showed good stability.

Practical Example 8

A mixture was prepared from 30 g (10.0 mmol of $NH_2$ groups) of a copolymer of a methyl (3-2-aminoethyl aminopropyl)siloxane and dimethylpolysiloxane represented by the following average structural formula:

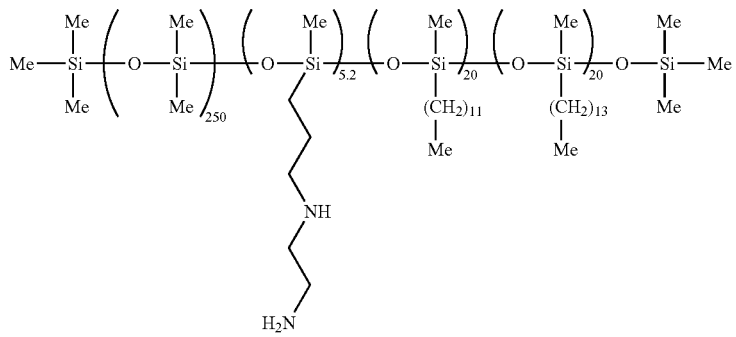

and 1.0 g (10.0 mmol) of an anhydrous succinic acid, which were both mixed in 36 g of isopropyl alcohol. The mixture was stirred for 5 hr at 30 to 40° C. Results of infrared (IR) analysis showed that specific absorption of carboxylic anhydride was lost, and that specific absorption of amide groups and carboxylic groups was detected. The obtained reaction product was cooled to the room temperature and further combined with 1.98 g (9.9 mmol) of a 20 wt. % aqueous solution of sodium hydroxide, and a reaction was carried out for 30 min. at room temperature. Following this, hexane was introduced and the solution was mixed uniformly. And, volatile contents were removed by distillation with heating in vacuum. As a result, a white solid substance was obtained. IR analysis showed that the obtained white solid substance was comprised of organically-modified methylpolysiloxane having carboxylic acid sodium salts on terminals of a silicon-bonded organic group and represented by the following formula:

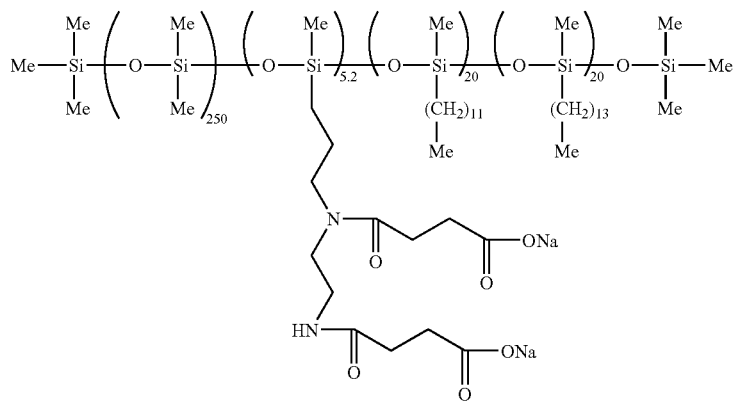

5 g of the obtained white solid substance (e.g. Gelling agent No. 8), 29.7 g of decamethylpentacyclosiloxane and 15.7 g of paraffin wax were stirred at 90° C. Then, the mixed solution was cooled, and a transparent hard gelatinous composition was obtained (The content of the gelling agent was 10 wt. %.).

Practical Example 9

A reaction and mixing was carried out under the same conditions as in Practical Example 8, but using 2.78 g (9.9 mmol) of 20 wt. % aqueous solution of potassium hydroxide in place of 20 wt. % aqueous solution of sodium hydroxide, and a white solid substance of an organically-modified methylpolysiloxane represented by the formula given below was obtained.

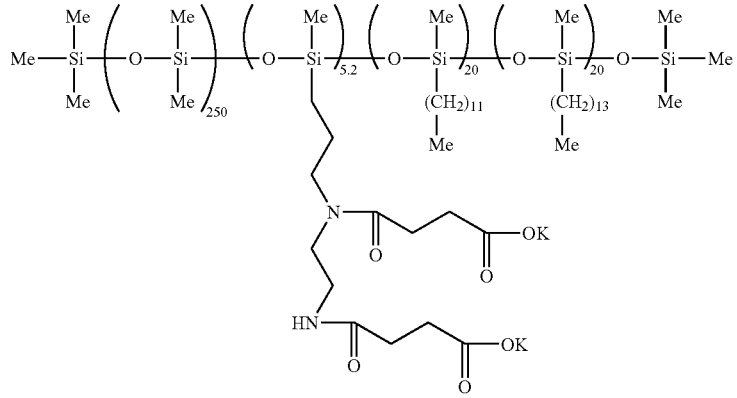

2 g of the obtained white solid substance (e.g. Gelling agent No. 9) and 18 g of liquid paraffin were stirred at 90° C. Then, the mixed solution was cooled, and a transparent hard gelatinous composition was obtained. This gelatinous composition kept its transparency superior to that of the sodium-salt type composition obtained in Practical Example 8, and had the feel of a soft gel.

After being stored for 3 months at room temperature, the product remained transparent and gelatinous and thus showed good stability.

Practical Example 10

A mixture was prepared from 30 g (9.5 mmol of NH2 groups) of a copolymer of methyl (3-aminopropyl)siloxane and dimethylpolysiloxane represented by the following average structural formula:

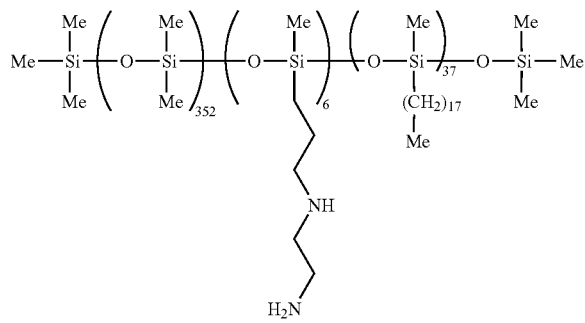

and 1.01 g (10.2 mmol) of an anhydrous succinic acid, which were both mixed in 36 g of isopropyl alcohol. The mixture was stirred for 5 hr at 30 to 40° C. Results of infrared (IR) analysis showed that specific absorption of carboxylic anhydride was lost, and that specific absorption of amide groups and carboxylic groups was detected. Then, the obtained reaction product was further combined with 2.02 g (10.1 mmol) of a 20 wt. % aqueous solution of sodium hydroxide, and a reaction was carried out for 30 min at 25° C. Following this, hexane was introduced and the solution was mixed uniformly. And, volatile contents were removed by distillation with heating in vacuum. As a result, a white solid substance was obtained. IR analysis showed that the obtained white solid substance was comprised of organically-modified methylpolysiloxane having carboxylic acid sodium salts on terminals of a silicon-bonded organic group and represented by the following formula:

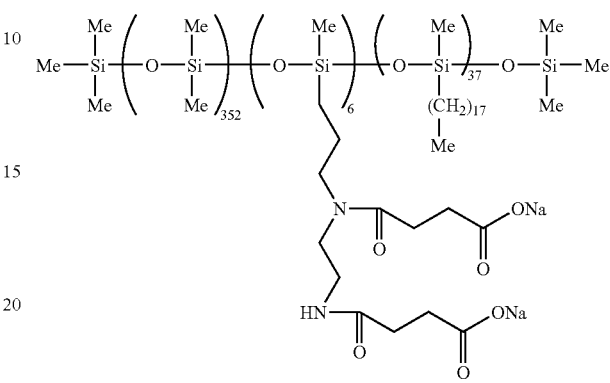

5 g of the obtained white solid substance (e.g. Gelling agent No. 10), 29.7 g of decamethylpentacyclosiloxane and 15.7 g of paraffin wax were stirred at 90° C. Then, the mixed solution was cooled, and a transparent hard gelatinous composition was obtained (The content of the gelling agent was 10 wt. %.). After being stored for 3 months at room temperature, the product remained transparent and gelatinous and thus showed good stability.

Practical Example 11

A mixture was prepared from the following components: 10 g of the organically-modified methylpolysiloxane obtained in Practical Example 7 having a sodium salt of a carboxylic acid on the molecular terminals of silicon-bonded organic groups; 10 g of isopropyl alcohol, 5 g of water, and 0.56 g of calcium chloride. The components were mixed for 4 hours with heating at 60° C. The reaction solution was combined with 200 g of hexane and water, and an inorganic salt formed in this process was washed. Then, the organic layer was removed, and a white solid substance of an organically-modified methylpolysiloxane represented by the formula given as below was obtained.

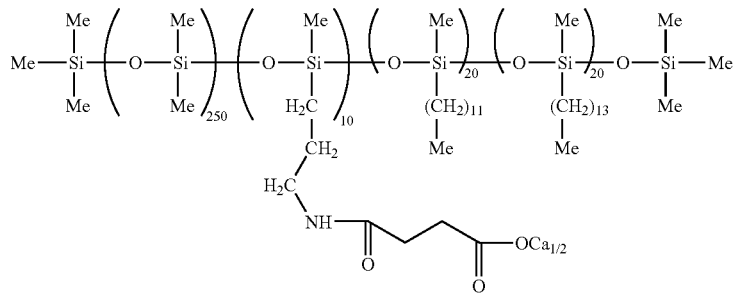

5 g of the obtained white solid substance (e.g. Gelling agent No. 11), 29.7 g of decamethylpentacyclosiloxane and 15.7 g of paraffin wax were stirred at 90° C. Then, the mixed solution was cooled, and a transparent hard gelatinous composition was obtained. After being stored for 3 months at room temperature, the product remained transparent and gelatinous and thus showed good stability.

Practical Example 12

A mixture was prepared from component (A) as a gelling agent obtained in aforementioned Practical Example 2 (e.g. Gelling agent No. 2), component (B) as a dimethylpolysiloxane capped at both molecular terminals with trimethylsiloxy group (viscosity: 6 mm²/s), toluene, hexane, isoparaffin, and isododecane. After the both components were stirred at 90° C., and the mixed solution was cooled to obtain gelatinous composition. As a result, gelatinous compositions shown in below Table 1 and table 2 were obtained.

Numbers in the tables are given in wt. %; symbol ◉ corresponds to a hard transparent gel, and symbol ○ corresponds to a soft transparent gel.

TABLE 1

| Gelatinous composition | | (a) | (b) | (c) | (d) | (e) |
|---|---|---|---|---|---|---|
| (A) | Gelling Agent No. 2 | 10 | 10 | 10 | 10 | 10 |
| (B) | Dimethylpolysiloxane capped at both molecular terminals with trimethylsiloxy groups (6 mm²/s) | 90 | | | | |
| | Toluene | | 90 | | | |
| | Hexane | | | 90 | | |
| | Isoparaffin | | | | 90 | |
| | Isododecane | | | | | 90 |
| Appearance of the gelatinous composition | | ◉ | ◉ | ◉ | ◉ | ◉ |

TABLE 2

| Gelatinous composition | | (a') | (b') | (c') | (d') | (e') |
|---|---|---|---|---|---|---|
| (A) | Gelling Agent No. 2 | 7.5 | 7.5 | 7.5 | 7.5 | 7.5 |
| (B) | Dimethylpolysiloxane capped at both molecular terminals with trimethylsiloxy groups (6 mm²/s) | 92.5 | | | | |
| | Toluene | | 92.5 | | | |
| | Hexane | | | 92.5 | | |
| | Isoparaffin | | | | 92.5 | |
| | Isododecane | | | | | 92.5 |
| Appearance of the gelatinous composition | | ○ | ○ | ○ | ○ | ○ |

Practical Example 13

A mixture was prepared from component (A) as a gelling agent obtained in aforementioned Practical Example 8 (e.g. Gelling agent No. 8), component (B) as a dimethylpolysiloxane capped at both molecular terminals with trimethylsiloxy group (viscosity: 6 mm²/s), toluene, liquid paraffin, isoparaffin, and isododecane. After the both components were stirred at 90° C., and the mixed solution was cooled to obtain gelatinous composition. As a result, gelatinous compositions shown in below Table 3 and Table 4 were obtained.

Numbers in the tables are given in wt. %; symbol ◉ corresponds to a hard transparent gel, and symbol ○ corresponds to a soft transparent gel.

TABLE 3

| Gelatinous composition | | (a) | (b) | (c) | (d) | (e) |
|---|---|---|---|---|---|---|
| (A) | Gelling Agent No. 8 | 10 | 10 | 10 | 10 | 10 |
| (B) | Dimethylpolysiloxane capped at both molecular terminals with trimethylsiloxy groups (6 mm²/s) | 90 | | | | |
| | Liquid paraffin | | 90 | | | |
| | Hexane | | | 90 | | |
| | Isoparaffin | | | | 90 | |
| | Isododecane | | | | | 90 |
| Appearance of the gelatinous composition | | ◉ | ◉ | ◉ | ◉ | ◉ |

TABLE 4

| Gelatinous composition | | (a') | (b') | (c') | (d') | (e') |
|---|---|---|---|---|---|---|
| (A) | Gelling Agent No. 8 | 7.5 | 7.5 | 7.5 | 7.5 | 7.5 |
| (B) | Dimethylpolysiloxane capped at both molecular terminals with trimethylsiloxy groups (6 mm²/s) | 92.5 | | | | |
| | Liquid paraffin | | 92.5 | | | |
| | Hexane | | | 92.5 | | |
| | Isoparaffin | | | | 92.5 | |
| | Isododecane | | | | | 92.5 |
| Appearance of the gelatinous composition | | ○ | ○ | ○ | ○ | ○ |

Comparative Example 1

A mixture was prepared from 10 g (2.82 mmol of $NH_2$ groups) of a copolymer of a methyl (3-2-aminoethyl aminopropyl)siloxane and dimethylpolysiloxane represented by the following average structural formula:

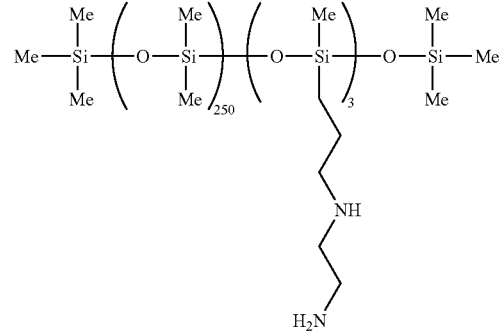

and 0.25 g (2.52 mmol) of an anhydrous succinic acid, which were both mixed in g of ethanol. The mixture was stirred for 5 hr at 30 to 35° C. Results of infrared (IR) analysis showed that specific absorption of carboxylic anhydride was lost, and that specific absorption of amide groups and carboxylic groups was detected. The reaction product was combined with 20 g of decamethylpentacyclosiloxane. After removal of the ethanol by distillation under reduced pressure, a liquid of low viscosity was obtained. This liquid comprised a mixture of decamethylpentacyclosiloxane and an organically-modified methylpolysiloxane represented by the following average structural formula:

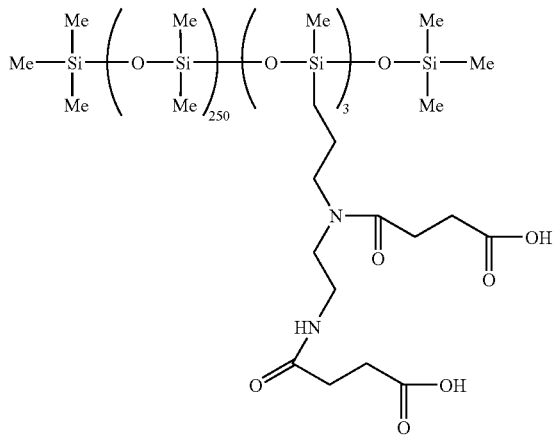

where concentration of the aforementioned organically-modified methylpolysiloxane was 20 wt. %. The mixed composition was cooled to room temperature (25° C.) but remained liquid, and no gelatinous composition was obtained.

Comparative Example 2

A mixture was prepared from 5 g (2.52 mmol of NH2 groups) of a copolymer of methyl (3-aminopropyl)siloxane and dimethylpolysiloxane represented by the following average structural formula:

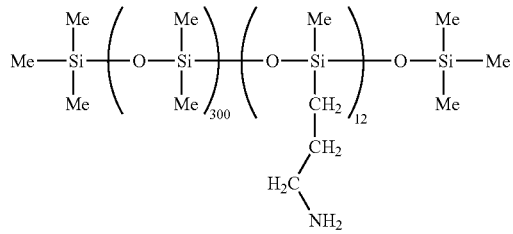

and 0.25 g (2.52 mmol) of an anhydrous succinic acid, which were both mixed in 5 g of ethanol. The mixture was stirred for 5 hr at 30 to 35° C. Results of infrared (IR) analysis showed that specific absorption of carboxylic anhydride was lost, and that specific absorption of amide groups and carboxylic groups was detected. The obtained reaction product was further combined with 0.15 g (2.52 mmol) of 2-aminoalcohol, and a reaction was carried out for 1.0 Hr. at 70° C. Following this, ethanol was removed by distillation with heating in vacuum. As a result, a white solid substance was obtained. IR analysis showed that the obtained white solid substance was comprised of organically-modified methylpolysiloxane having carboxylic acid (2-amino alcohol) salts on terminals of a silicon-bonded organic group and represented by the following formula:

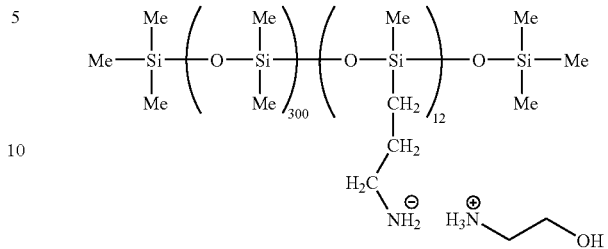

5 g of the obtained white solid substance, 29.7 g of decamethylpentacyclosiloxane and 15.7 g of paraffin wax were stirred at 90° C. The mixed composition was cooled to room temperature (25° C.) but remained liquid, and no gelatinous composition was obtained.

Practical Example 14

Results of the measurement of viscoelastic properties of gelatinous compositions obtained in Practical Example 1, Practical Example 2, and Practical Example 3 are shown in FIG. 1. In this figure, f designates frequency (Hz), G' designates storage modulus of elasticity, and η designates viscosity coefficient.

It can be seen from FIG. 1 that as the frequency increases, viscosity coefficient (η) of the gelatinous composition decrease. This shows the thixotropic, viscoelastic characteristics of the composition. Furthermore, the gelatinous composition of Practical examples 1 to 3 are characterized by a high storage modulus of elasticity (G').

Practical Example 15

A mixture was prepared from 7.5 wt % of a gelling agent obtained in aforementioned Practical Example 10 (e.g. Gelling agent No. 10), 60.5 wt % of decamethylpentacyclosiloxane and cosmetic oil compounds given in the below table (paraffin wax, tri caprylic/capric glyceride ester, trioctanoine, phenyltrimethicone, and scwaran). After these components were stirred for 2 Hr at 80° C., and the mixed solution was cooled to obtain gelatinous composition. As a result, the appearance and refractive index of gelatinous compositions was shown in below Table 5. Furthermore, results of the measurement of viscoelastic properties of gelatinous compositions obtained in Pr.Ex. 15-1, Pr.Ex. 15-2, and Pr.Ex. 15-3 are shown in FIG. 2 to FIG. 5. In this figure, f designates frequency (Hz), G' designates storage modulus of elasticity, and η designates viscosity coefficient.

It can be seen from FIG. 2 to FIG. 5 that as the frequency increases, viscosity coefficient (η) of the gelatinous composition decrease. This shows the thixotropic, viscoelastic characteristics of the composition. Furthermore, these gelatinous compositions are characterized by a high storage modulus of elasticity (G').

TABLE 5

| Pr. Ex. | Gelling agent | cosmetic oil compounds | appearance | refractive index |
|---|---|---|---|---|
| 15-1 | No. 10 | paraffin wax | transparent gel | 1.4237 |
| 15-2 | No. 10 | tri caprylic/capric glyceride ester | transparent gel | 1.4171 |

| Pr. Ex. | Gelling agent | cosmetic oil compounds | appearance | refractive index |
|---|---|---|---|---|
| 15-3 | No. 10 | trioctanoine | transparent gel | 1.4153 |
| 15-4 | No. 10 | phenyltrimethicone | transparent gel | 1.4179 |
| 15-5 | No. 10 | scwaran | transparent gel | 1.4196 |

INDUSTRIAL APPLICABILITY

The gelling agent of the present invention is useful to obtain a gel composition comprising of silicone oils, in particular, hydrophobic silicone oils, non-polar organic compounds, and low-polarity organic compounds. Furthermore, the gelatinous composition of the invention may be used for the preparation of such liquid and paste-like items as various industrial products, pharmaceutical products, cosmetics, hair care products, and household care products. These products are characterized by good tactile feel, pleasant feel of use and its preservation stability. The gelatinous composition of the invention may be used in the form of car waxes, surface-treating agents, mold-release agents, lubricants, resin additives, and emulsion stabilizers.

The invention claimed is:

1. A gelling agent comprising an organopolysiloxane having a silicon-bonded organic group Y represented by general formula (1) and an optionally substituted $C_9$ or more univalent hydrocarbon group Z:

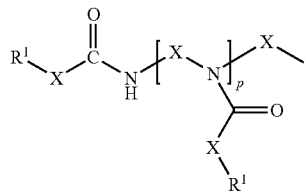

(1)

wherein $R^1$ designates a group containing metal salt of a carboxylic acid represented by formula —COO$^-$($M^{n+}$)$_{1/n}$, where M is a metal that has a valence of 1 or higher, and n is the valence of M; X's designate the same or different $C_2$ to $C_{14}$ bivalent hydrocarbon groups;
p designates an integer from 0 to 10;
wherein the organopolysiloxane is a linear-chain organopolysiloxane represented by general formula (3):

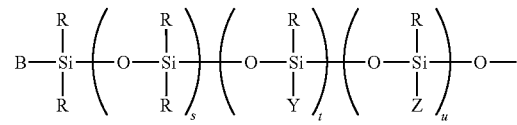

(3)

wherein R is a $C_1$ to $C_8$ alkyl group except for the organic group represented by general formula (1), Y designates an organic group of general formula (1), B is R, Y or Z, the subscript "s" designates an integer in the range of 10 to 100,000, "t" designates an integer between 0 and 50, and "u" designates an integer between 0 and 1000, and wherein when t=0, at least one of the two B's is Y, when u=0, at least one of the two B's is Z, and when t=0 and u=0, one of the two B's is Y and another is Z; and wherein (s+t+u) is an integer from 20 to 5000, {t/(s+t+u)} is in the range of 0.001 to 0.05, and {u/(s+t+u)} is in the range of 0.001 to 0.30.

2. A gelling agent comprising an organopolysiloxane having a silicon-bonded organic group Y represented by general formula (1) and an optionally substituted $C_9$ or more univalent hydrocarbon group Z:

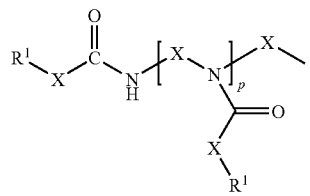

(1)

wherein $R^1$ designates a group containing metal salt of a carboxylic acid represented by formula —COO$^-$($M^{n+}$)$_{1/n}$, where M is a metal that has a valence of 1 or higher, and n is the valence of M; X's designate the same or different $C_2$ to $C_{14}$ bivalent hydrocarbon groups;
p designates an integer from 0 to 10.

3. A gelling agent comprising an organopolysiloxane having a silicon-bonded organic group Y represented by general formula (1) and an optionally substituted $C_9$ or more univalent hydrocarbon group Z:

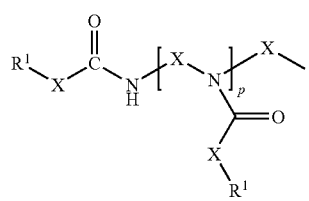

(1)

wherein $R^1$ designates a group containing metal salt of a carboxylic acid represented by formula —COO$^-$($M^{n+}$)$_{1/n}$, where M is a metal that has a valence of 1 or higher, and n is the valence of M; X's designate the same or different $C_2$ to $C_{14}$ bivalent hydrocarbon groups; and
p designates an integer from 0 to 10;
wherein the organopolysiloxane is a linear-chain organopolysiloxane represented by general formula (3):

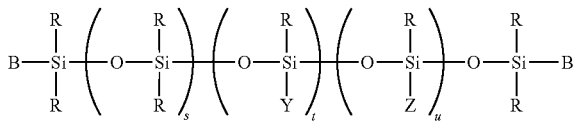

(3)

wherein R is a $C_1$ to $C_8$ alkyl group except for the organic group represented by general formula (1), Y designates an organic group of general formula (1), B is R, Y or Z, the subscript "s" designates an integer in the range of 10 to 100,000, "t" designates an integer between 0 and 50, and "u" designates an integer between 0 and 1000, and wherein when t=0, at least one of the two B's is Y, when u=0, at least one of the two B's is Z, and when t=0 and u=0, one of the two B's is Y and another is Z; and wherein (s+t+u) is an integer from 20 to 5000, $\{t/(s+t+u)\}$ is in the range of 0.001 to 0.05, and $\{u/(s+t+u)\}$ is in the range of 0.001 to 0.30.

4. The gelling agent according to claim 2, wherein the organopolysiloxane is a linear-chain organopolysiloxane represented by general formula (3):

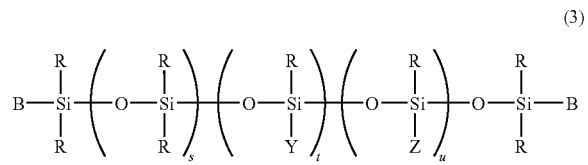
(3)

wherein R designates an optionally substituted $C_1$ to $C_8$ univalent hydrocarbon group except for the organic group represented by general formula (1), Y designates an organic group of general formula (1), B is R, Y or Z, the subscript "s" designates an integer in the range of 10 to 100,000, "t" designates an integer between 0 and 50, and "u" designates an integer between 0 and 1000, and wherein when t=0, at least one of the two B's is Y, when u=0, at least one of the two B's is Z, and when t=0 and u=0, one of the two B's is Y and another is Z.

5. The gelling agent according to claim 2, wherein M is an alkali metal and X is an alkylene group.

6. A gelatinous composition comprising:
99 wt. % of gelling agent according to claims 2; and
(B) 99 to 1 wt. % of a compound selected from the group consisting of a silicone oil, a non-polar organic compound, a low-polar organic compound, or mixtures thereof.

7. The gelatinous composition according to claim 6, wherein the silicone oil is a hydrophobic silicone oil.

8. The gelatinous composition according to claim 6, wherein the silicone oil is a volatile silicone oil.

9. The gelatinous composition according to claim 6, wherein the refractive index of the gelatinous composition is in the range of 1.20 to 1.60.

10. The gelling agent according to claim 3, wherein M is an alkali metal and X is an alkylene group.

11. A gelatinous composition comprising:
(A) 99 wt. % of gelling agent according to claims 3; and
(B) 99 to 1 wt. % of a compound selected from the group consisting of a silicone oil, a non-polar organic compound, a low-polar organic compound, or mixtures thereof.

12. The gelatinous composition according to claim 11, wherein the silicone oil is a hydrophobic silicone oil.

13. The gelatinous composition according to claim 11, wherein the silicone oil is a volatile silicone oil.

14. The gelatinous composition according to claim 11, wherein the refractive index of the gelatinous composition is in the range of 1.20 to 1.60.

* * * * *